United States Patent
Kim et al.

(10) Patent No.: US 11,298,267 B2
(45) Date of Patent: *Apr. 12, 2022

(54) SYSTEM FOR INNER EAR DRUG DELIVERY VIA TRANS-ROUND WINDOW MEMBRANE INJECTION

(71) Applicants: The Charles Stark Draper Laboratory, Inc., Cambridge, MA (US); Massachusetts Eye and Ear Infirmary, Boston, MA (US)

(72) Inventors: Ernest S. Kim, Cambridge, MA (US); Michael McKenna, Boston, MA (US); Ruwan Kiringoda, Boston, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 64 days.

This patent is subject to a terminal disclaimer.

(21) Appl. No.: 16/272,395

(22) Filed: Feb. 11, 2019

(65) Prior Publication Data
US 2019/0167480 A1    Jun. 6, 2019

Related U.S. Application Data

(63) Continuation of application No. 15/629,279, filed on Jun. 21, 2017, now Pat. No. 10,201,455.
(Continued)

(51) Int. Cl.
*A61F 11/00* (2006.01)
*A61M 5/142* (2006.01)
*A61M 31/00* (2006.01)

(52) U.S. Cl.
CPC ............. *A61F 11/00* (2013.01); *A61M 5/142* (2013.01); *A61M 31/00* (2013.01); *A61M 2210/0662* (2013.01)

(58) Field of Classification Search
CPC ....... A61F 11/00; A61M 31/00; A61M 5/142; A61M 2210/0662
See application file for complete search history.

(56) References Cited

U.S. PATENT DOCUMENTS

| 10,201,455 B2* | 2/2019 | Kim ...................... A61M 31/00 |
| 2004/0172005 A1* | 9/2004 | Arenberg ................ A61F 11/00 604/514 |

(Continued)

FOREIGN PATENT DOCUMENTS

| JP | 2001-515371 | 9/2001 |
| JP | 2008-537684 | 9/2008 |

(Continued)

OTHER PUBLICATIONS

Fujita, Takeshi, "Surgical Anatomy of the Human Round Window Region: Implication for Cochlear Endoscopy Through the Extrnal . . . " Copyright 2016, Otology & Neurotology, Inc. dated May 2016, 1-7 pages.
(Continued)

*Primary Examiner* — Amber R Stiles
(74) *Attorney, Agent, or Firm* — Foley & Lardner LLP (57) ABSTRACT

The present disclosure discussed a handpiece for trans-canal delivery of a therapeutic substance to the inner ear. The handpiece can be inserted into the middle ear via a surgical tympanotomy approach. The handpiece can enable a controlled injection of a therapeutic substance directly through the round window membrane and into the inner ear. The direct delivery of the therapeutic substance to the inner ear can enable the delivery of a precise amount of therapeutic substance into the inner ear. Because the therapeutic substance is delivery directly to the inner ear the delivery of the therapeutic substance is not subject to limitations on molecule size and inconsistent diffusion rates that are present
(Continued)

when therapeutic substances are diffused across the round window membrane.

18 Claims, 10 Drawing Sheets

Related U.S. Application Data (60) Provisional application No. 62/353,324, filed on Jun. 22, 2016.

(56) References Cited

U.S. PATENT DOCUMENTS

| | | | |
|---|---|---|---|
| 2005/0240147 A1 | 10/2005 | Makower et al. | |
| 2008/0065002 A1* | 3/2008 | Lobl | A61M 25/0074 604/21 |
| 2010/0030130 A1 | 2/2010 | Parker et al. | |
| 2010/0106134 A1* | 4/2010 | Jolly | A61M 31/002 604/506 |

FOREIGN PATENT DOCUMENTS

| | | |
|---|---|---|
| JP | 2010-268963 | 12/2010 |
| WO | WO-00/04854 | 2/2000 |
| WO | WO-00/33775 | 6/2000 |
| WO | WO-2008/030485 | 3/2008 |
| WO | WO-2010/045432 | 4/2010 |

OTHER PUBLICATIONS

International Search Report and Written Opinion for PCT/US2017/038532 dated Sep. 28, 2017.
Notice of Allowance on U.S. Appl. No. 15/629,279 dated Oct. 1, 2018.
Swan, E.E.L., Mescher, M.J., Sewell, W.F., Tao, S.L. and Borenstein, J.T., 2008. Inner ear drug delivery for auditory applications. Advanced drug delivery reviews, 60(15), p. 1583-1599.
Foreign Action other than Search Report on EP 17734925.5 dated Aug. 6, 2021.
Japanese Office Action on JP Appln. 2018-567614 dated Apr. 22, 2021.

* cited by examiner

SYSTEM FOR INNER EAR DRUG DELIVERY VIA TRANS-ROUND WINDOW MEMBRANE INJECTION

CROSS-REFERENCE TO RELATED APPLICATION

The present application claims the benefit of priority 35 U.S.C. § 120 as a continuation of U.S. patent application Ser. No. 15/629,279, filed Jun. 21, 2017, which claims the benefit of priority under 35 U.S.C. § 119 to U.S. Provisional Patent Application No. 62/353,324, filed Jun. 22, 2016. The foregoing applications are herein incorporated by reference in their entirety.

BACKGROUND OF THE DISCLOSURE

Delivery of therapeutics to the human inner ear can be challenging for clinicians. Two anatomic "windows" from the middle ear to the inner ear exist, the oval and round windows. Each of these windows include a semi-permeable membrane. Drug delivery to the inner ear requires that a therapeutic substance cross one of these membranes.

SUMMARY OF THE DISCLOSURE

Inner ear drug delivery can use diffusion to cross one or both of the membranes of the anatomic windows to the inner ear. Relying on diffusion across a membrane poses a number of difficulties. For example, diffusing therapeutic substances across the membranes can introduce a lack of precision in terms of dose delivery. Relying on diffusion can also limit the size and characteristics of therapeutic substance's molecules because, for example, not all substances can diffuse across the membranes. Another example challenge is that the round window membrane permeability can vary between patients or during states of inflammation. The handpiece of the present disclosure can overcome these challenges by delivering a therapeutic substance directly to the inner ear.

According to an aspect of the disclosure, a handpiece to deliver a fluid to an ear includes a tool shaft. The tool shaft includes a first distal end, a first proximal end, a first fluidic channel, and a first longitudinal axis. The handpiece also includes an angled portion. The angled portion includes a second distal end, a second proximal end coupled with the first distal end, a second fluidic channel in communication with the first fluidic channel, and a second longitudinal axis that defines an angle with the first longitudinal axis. The angled of the angled portion is configured for trans-canal positing of a tip portion at a round window. The handpiece also includes the tip portion that projects from the angled portion. The tip portion includes an outlet and a third fluidic channel in communication with the second fluidic channel. The handpiece includes a collar that is coupled with the tip portion a predetermined distance from the outlet. The collar is configured to seat with the round window and control a distance the tip portion projects into a cochlea.

The handpiece can also include a fluid reservoir in communication with the outlet via the first fluidic channel, the second fluidic channel, and the third fluidic channel. The fluid reservoir further can include a pierceable septum configured to enable filling of the fluid reservoir.

In some implementations, the handpiece can include a fluid reservoir. The handpiece can also include a self-contained pumping system that is coupled with the tool shaft. The self-contained pumping system can be configured to pump a fluid from the fluid reservoir to the outlet.

The first fluidic channel, the second fluidic channel, and the third fluidic channel form a fluid channel. The fluid channel can be a continuous fluid channel. The angled portion can be configured to detach from the tool shaft. The angled portion can be configured to rotate with respect to the tool shaft. The tip portion can be configured to rotate with respect to the angled portion. The tip portion can be configured to detach from the angled portion. The collar can be substantially dome shaped.

The first fluid channel can be encased within the tool shaft. The second fluid channel can be encased within the angled portion. The third fluid channel can be encased within the tip portion. Each of the first fluid channel, the second fluid channel, and the third fluid channel can be encased in a sterilizable plastic or metal.

In some implementations, the angle between the tip portion and the angled portion can be between about 140° and about 170°. The tip portion can project from the angled portion at an angle between about 75° and about 130°. The tip portion can project from the angled portion at an angle between about 110° and about 120°.

According to an aspect of the disclosure, a method can include providing a handpiece. The handpiece can include a tool shaft. The tool shaft includes a first distal end, a first proximal end, a first fluidic channel, and a first longitudinal axis. The handpiece also includes an angled portion. The angled portion includes a second distal end, a second proximal end coupled with the first distal end, a second fluidic channel in communication with the first fluidic channel, and a second longitudinal axis that defines an angle with the first longitudinal axis. The angled of the angled portion is configured for trans-canal positing of a tip portion at a round window. The handpiece also includes the tip portion that projects from the angled portion. The tip portion includes an outlet and a third fluidic channel in communication with the second fluidic channel. The handpiece includes a collar that is coupled with the tip portion a predetermined distance from the outlet. The collar is configured to seat with the round window and control a distance the tip portion projects into a cochlea. The method can include piercing a round window membrane with the tip portion of the handpiece. The method can include flowing a fluid through the outlet and into a cochlea via the first fluidic channel, the second fluidic channel, and the third fluidic channel.

The method can include forming a ventilation hole in the stapes footplate. The method can include flowing, by a self-contained pumping system coupled with the tool shaft, the fluid from a reservoir. The method can include seating the collar in the round window. The method can include setting a rotational offset between the tip portion and the angled portion.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure discussed a handpiece for transcanal delivery of a therapeutic substance to the inner ear. The handpiece can be inserted into the middle ear via a surgical tympanotomy approach. The handpiece can enable a controlled injection of a therapeutic substance directly through the round window membrane and into the inner ear. The direct delivery of the therapeutic substance to the inner ear can enable the delivery of a precise amount of therapeutic substance into the inner ear. Because the therapeutic substance is delivery directly to the inner ear the delivery of the therapeutic substance is not subject to limitations on molecule size and inconsistent diffusion rates that are present when therapeutic substances are diffused across the round window membrane.

Figure 1:
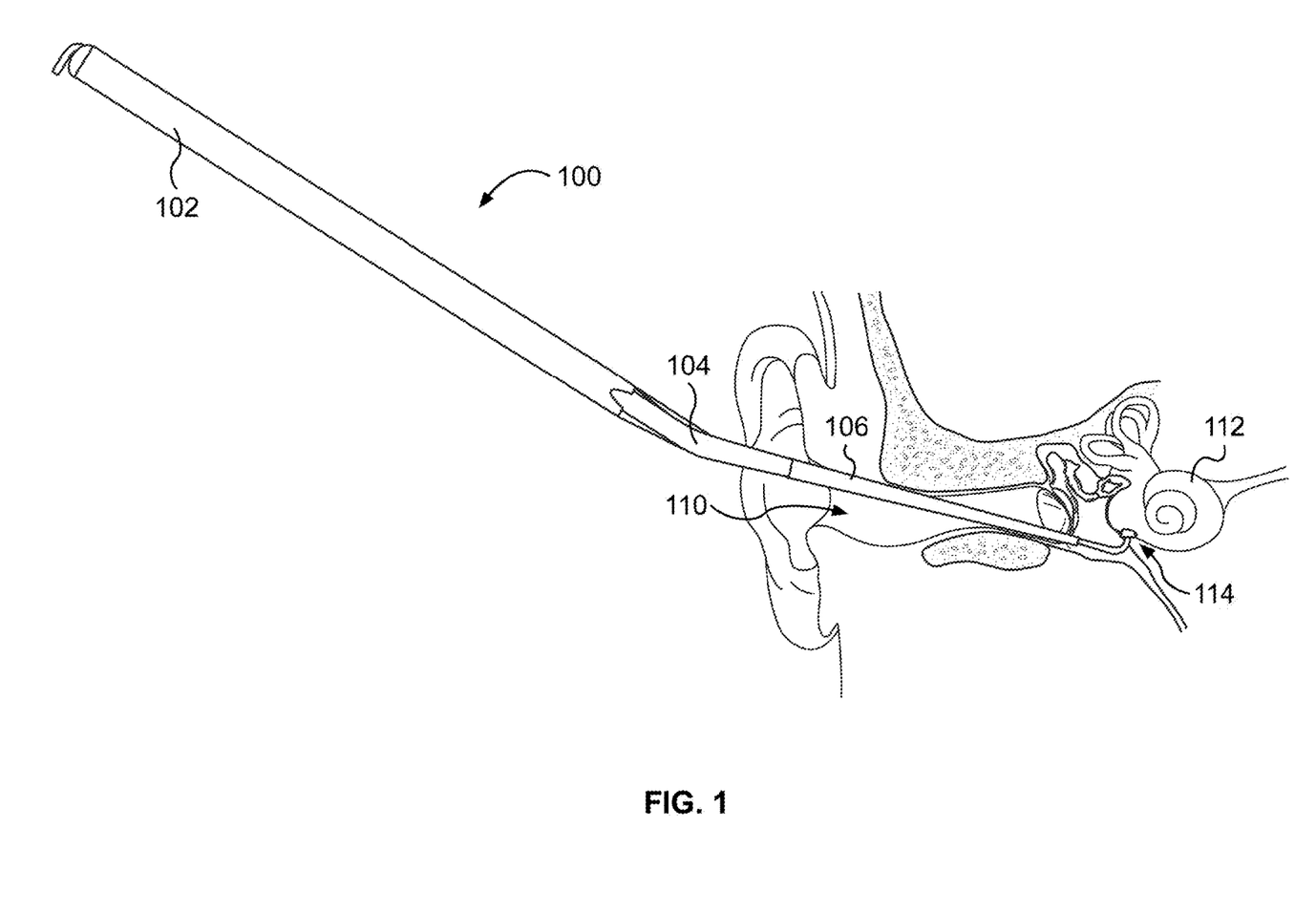
FIG. 1 illustrates an example handpiece delivering fluid to the inner ear of a patient.

FIG. 1 illustrates an example handpiece 100 delivering fluid to the inner ear of a patient. The fluid can be any therapeutic substance or therapeutic agent. The handpiece 100 includes a tool shaft 102, an angled portion 104, and a tip portion 106. The tip portion 106 can also include a collar 108. The handpiece 100 is inserted into the ear canal 110 of the patient for the transcanal delivery of fluid to the cochlea 112 via the round window 114. The tip portion 106 can be used to pierce the round window membrane to enable fluid to be delivered to the cochlea 112.

Figure 2:
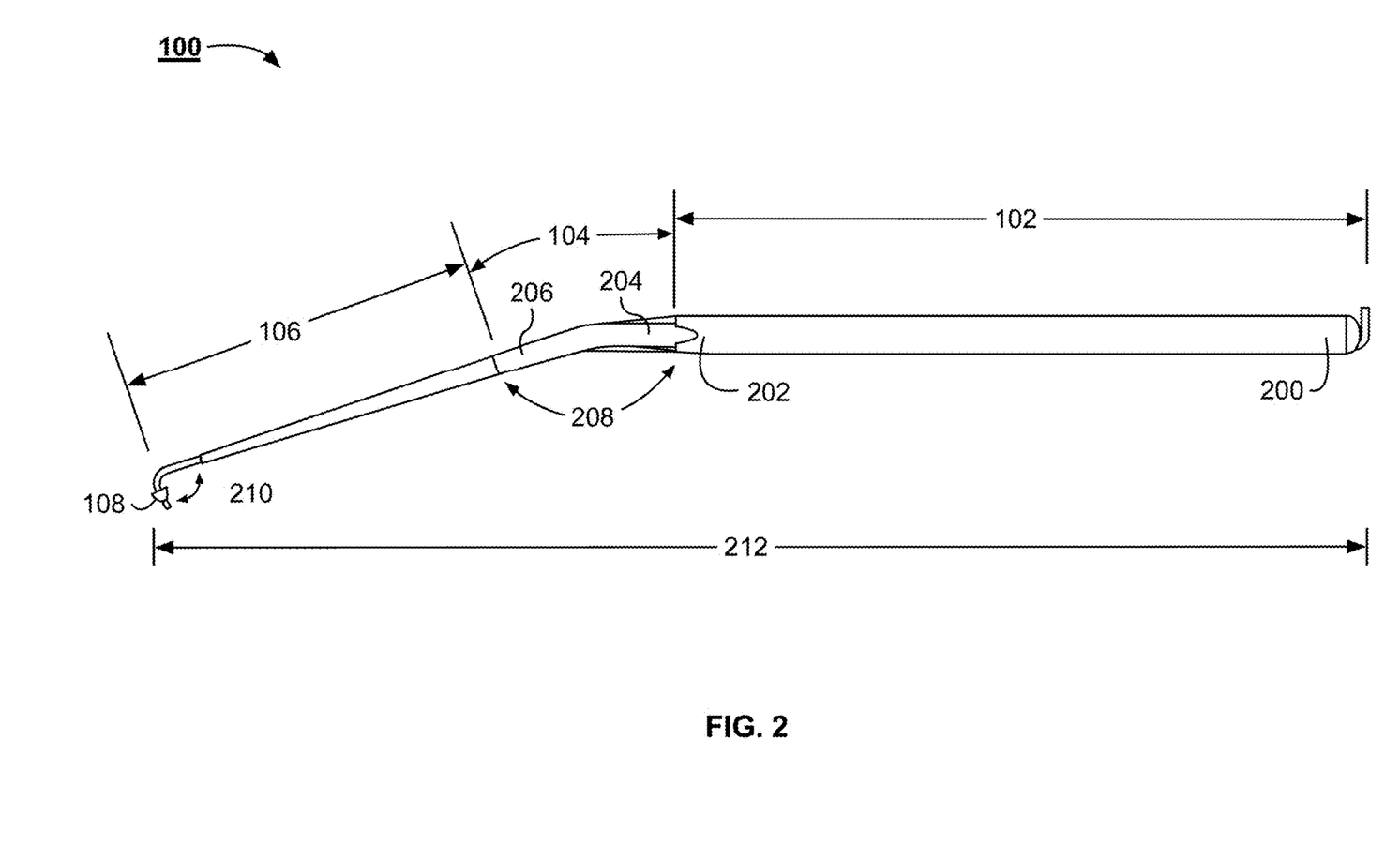
FIG. 2 illustrates a side view of the example handpiece illustrated in FIG. 1.

FIG. 2 illustrates a side view of the example handpiece 100. The handpiece 100 includes the tool shaft 102, the angled portion 104, and the tip portion 106. A surgeon can use the tool shaft 102 to hold and manipulate the handpiece 100 and position of the tip portion 106. The outer surface of the tool shaft 102 can include knurling to enable a better grip of the handpiece 100 by the surgeon. The tool shaft 102 includes a proximal end 200 and a distal end 202. The tool shaft 102 can have a diameter of about 4 mm, 5 mm, or about 6 mm. The tool shaft 102 can have a length of between about 90 mm and about 150 mm, between about 90 mm and about 130 mm, or between about 100 mm and about 120 mm. In some implementations, the length of the tool shaft 102 is 110 mm.

The distal end of the tool shaft 102 is coupled with the proximal end 204 of the angled portion 104. The tip portion 106 is coupled with the distal end 206 of the angled portion 104. The angled portion 104 is angled to enable the tip portion 106 to traverse the ear canal in a minimally invasive procedure and reach the round window. The angled portion 104 forms an angle 208 between the tool shaft 102 and the tip portion 106. The angle 208 can be about 170° and about 90°, between about 170° and about 110°, between about 170° and about 120°, between about 170° and about 140°, or between about 165° and about 155°. The angle 208 can be defined as the angle between a longitudinal axis of the tool shaft 102 and a longitudinal axis of the tip portion 106. The angle 208 is configured to enable transcanal positing of the tip portion 106 at a patient's round window. The angle 208 can be selected to enable a surgeon to position the tip portion 106 at the round window and provide the surgeon visual access to the ear canal.

The tip portion 106 can be coupled with the distal end 206 of the angled portion 104. The distal portion of the tip portion 106 can be angle. The angle 210 can be between about 70° and about 140°, between about 75° and about 130°, between about 90° and about 120°, between about 100° and about 120°, or between about 110° and about 120°. For example, the angle 210 can be about 105°, 106°, 107°, 108°, 109°, 110°, 111°, 112°, 113°, 114°, 115°, 116°, 117°, 118°, 119°, or 120°. The angle 210 can be selected to position the distal portion of the tip portion 106 substantially perpendicular to the round window when the handpiece 100 is inserted through the ear canal. The angle 210 can be selected based on the anatomical configuration of the patient's inner and middle ear. For example, the surgeon can select a handpiece 100 with an appropriate angle 210 based on the position and angle of the round window and the round window niche. In some implementations, the surgeon can determine which angle 210 to select using CT or MRI images of the middle and inner ear. The handpiece 100 can be manufactured with different angle 210 configurations. In some implementations, the surgeon can bend the tip portion 106 to alter the angle 210 during a procedure.

The tip portion 106 can include a collar 108. The collar 108 can be configured to seat within the round window. The collar 108 can seal the round window once the tip portion 106 pierces the round window membrane. The collar 108 can also control the depth the end of the tip portion 106 can be inserted into the cochlea. The collar 108 can include a medical-grade silicone. The collar 108 can be substantially domed or semi-spherical in shape. The diameter of the collar 108, at the collar's widest, can be between about 0.5 mm and about 3 mm, between about 0.5 mm and about 2.5 mm, between about 1 mm and about 2 mm, or between about 1.5 mm and about 2 mm.

The handpiece 100 can have an overall length 212 between about 130 mm and about 170 mm, between about 140 mm and about 160 mm, or between about 140 mm and about 150 mm. While described as different portions, the tool shaft 102, the angled portion 104, and the tip portion 106 can each be manufactured as single or multiple pieces. For example, the handpiece 100 can include one, two, or three separate pieces. The handpiece 100 can be separable at the interface between any of the tool shaft 102, the angled portion 104, and the tip portion 106. In some implementations, the interface between the tool shaft 102, the angled portion 104, and the tip portion 106 does not indicate that the portions are separatble. For example, the tool shaft 102, the angled portion 104, and the tip portion 106 can be manufactured as a single piece. In other implementations, the angled portion 104 and the tool shaft 102 can form a first piece and the tip portion 106 can form a second piece. In some implementations, the handpiece 100 is reusable. In other implementations, the handpiece 100 is disposable. The handpiece 100 can be manufactured from medically-approved sterilizable materials. For example, the handpiece 100 can be manufactured from 316 stainless steel or a sterilizable plastic.

Figure 3:
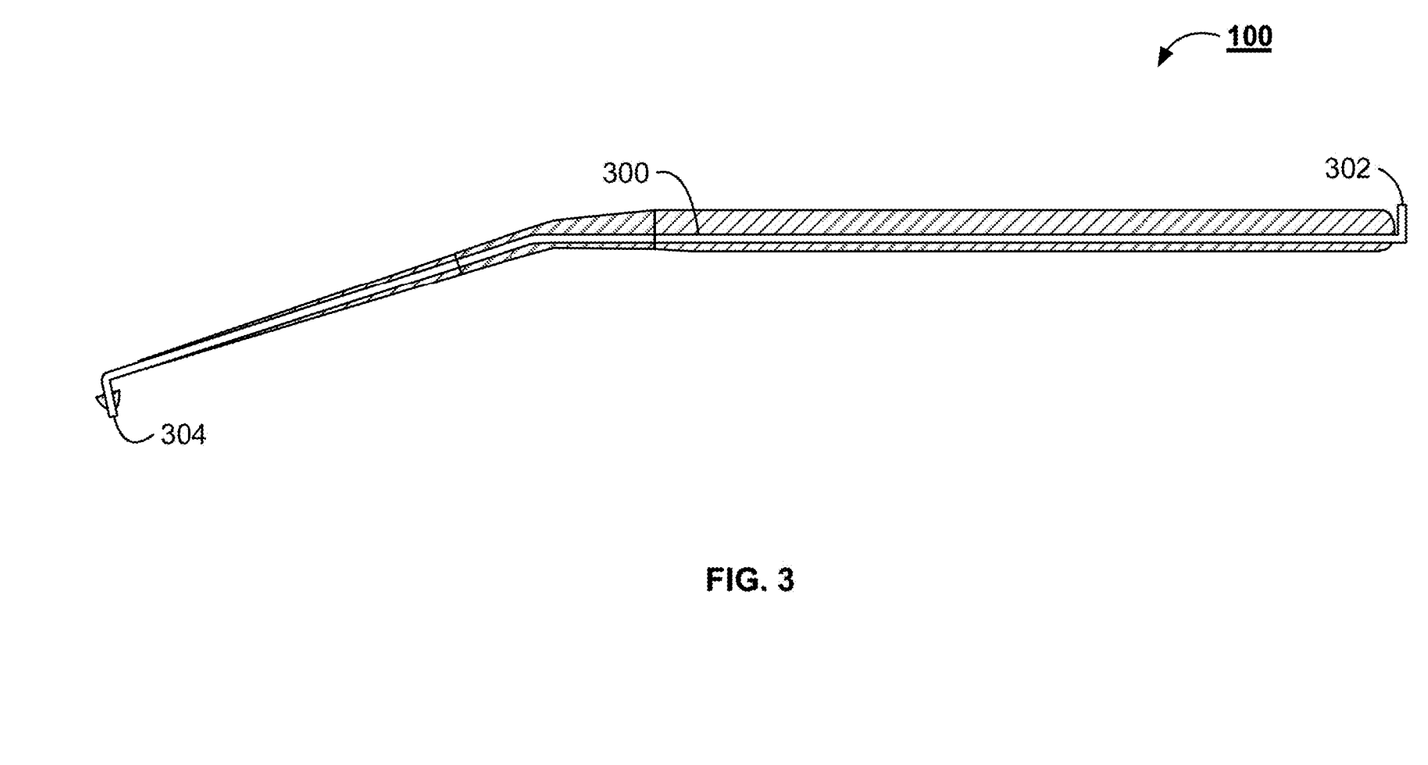
FIG. 3 illustrates a cross-sectional view of the example handpiece illustrated in FIG. 1.

FIG. 3 illustrates a cross-sectional view of the example handpiece 100. The handpiece 100 includes a microfluidic channel 300. The microfluidic channel 300 includes an inlet 302 and an outlet 304. The inlet 302 can be coupled with a reservoir. The reservoir is described further in relation to FIGS. 9 and 10. The microfluidic channel 300 can have a gauge of about 22. The microfluidic channel's gauge can be between about 12 and 28, between about 16 and about 24, between about 18 and about 22, or between about 20 and 22. The microfluidic channel 300 can have a dead volume of between about 10 μL and about 25 μL, between about 15 μL and about 25 μL, or between about 20 μL and about 25 μL.

Figure 4:
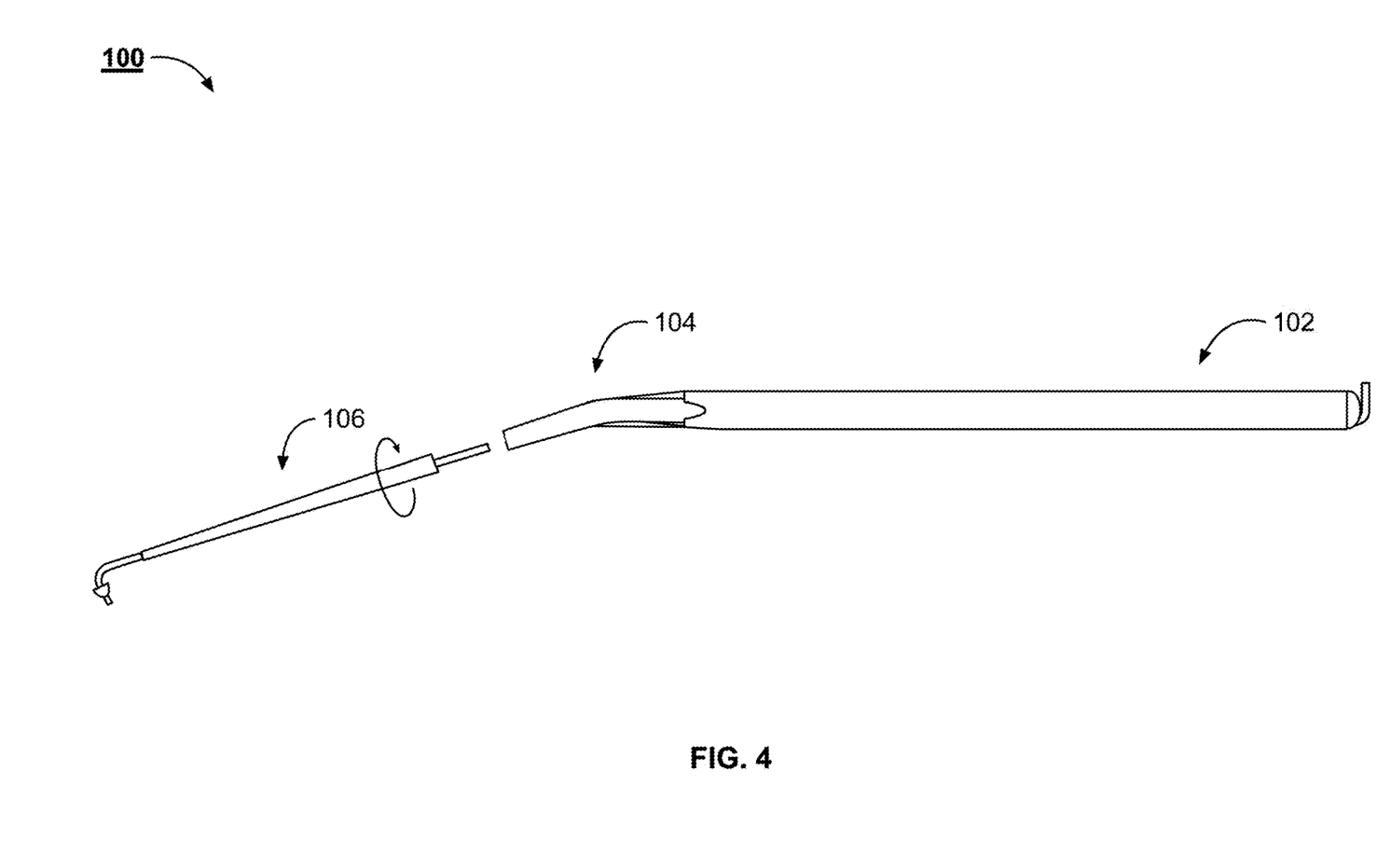
FIG. 4 illustrates a side view of the example handpiece illustrated in FIG. 1.

The microfluidic channel 300 can include different portions. For example, each of the tool shaft 102, angled portion 104, and the tip portion 106 can include a different portion of the microfluidic channel 300. The different portions can be a single channel, continuous channel. In some implementations, the microfluidic channel 300 is separable at the interface between one or more of the portions. In some implementations, the microfluidic channel portions are separable near the interface between the different portions of the handpiece 100. For example, the microfluidic channel portion within the tip portion 106 can extend past the tip portion 106 (as illustrated in FIG. 4) and the microfluidic channel portion within the angled portion 104 can stop prior to the distal end 206, such that portion of the microfluidic channel extending from the tip portion 106 can be received by the angled portion 104. In some implementations, the handpiece 100 can include a plurality of microfluidic channels 300. For example, the handpiece 100 can include different microfluidic channels 300 for delivering different therapeutic agents. In some implementations, a second microfluidic channel 300 can be used to evacuate fluid from the cochlea.

FIG. 4 illustrates a side view of the example handpiece 100. In some implementations, one or more of the portions of the handpiece 100 are separable from one another. FIG. 4 illustrates an example handpiece 100 with a separable tip portion 106. The tip portion 106 can be separated from the tool shaft 102 and the angled portion 104 to facilitate sterilization of the handpiece 100. The tip portion 106 can be separable from the angled portion 104 to enable the tip portion 106 to be recoupled with the angled portion 104 at a different rotational angle. The tip portion 106 can be rotated with respect to the angled portion 104 without separating the tip portion 106 from the angled portion 104. The tip portion 106 can be rotated with respect to the angled portion 104 to provide the surgeon with improved access to the round window. For example, the surgeon can adapt the default position of the tip portion 106 to account for variability between patient anatomies. The handpiece 100 can include gaskets or o-rings at the interface between the separable portions. The separable portions can be coupled together with snap-on connectors, friction-fit or press-fit connections, or Luer lock connections.

Figure 5:
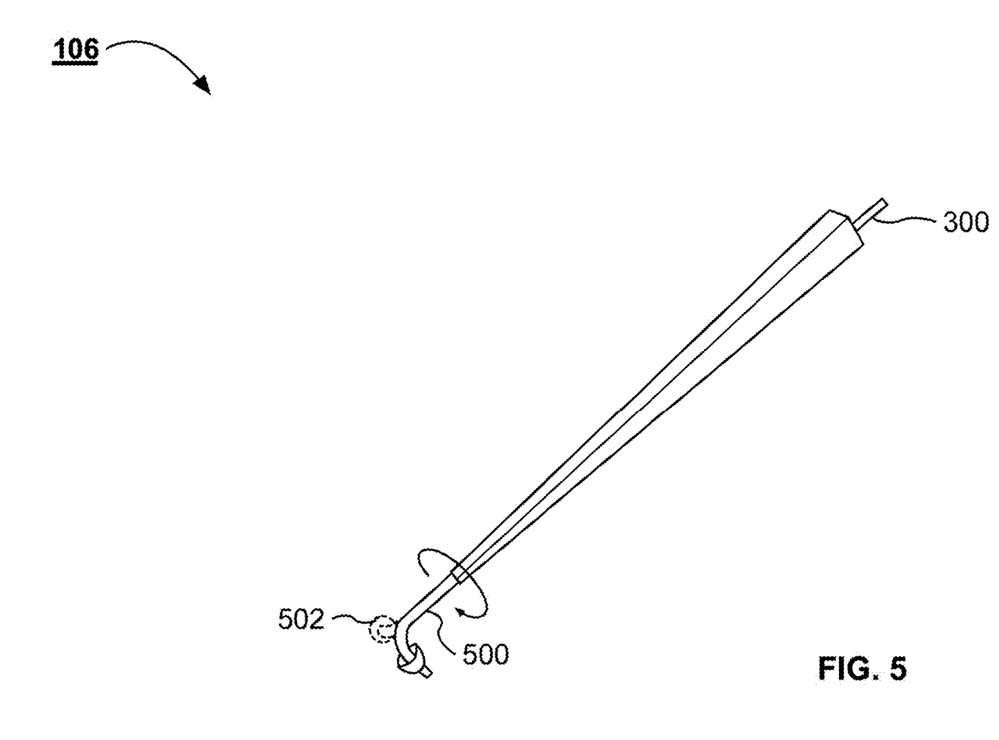
FIG. 5 illustrates an example tip portion for the handpiece illustrated in FIG. 1.

FIG. 5 illustrates an example tip portion 106 for the example handpiece 100. The tip portion 106 illustrated in FIG. 5 is separated from the angled portion 104 and the tool shaft 102 of the handpiece 100. The tip portion 106 can include a tip 500. The tip 500 can be portion of the microfluidic channel 300 extending from the body of the tip portion 106. In some implementations, all of the tip portion 106 can be rotated with respect to the angled portion 104. In other implementations, the tip 500 can be rotated within the tip portion 106. In either example, the tip 500 can be rotated from the position illustrated in FIG. 4 to a second position 502, illustrated by the dashed lines.

Figure 6:
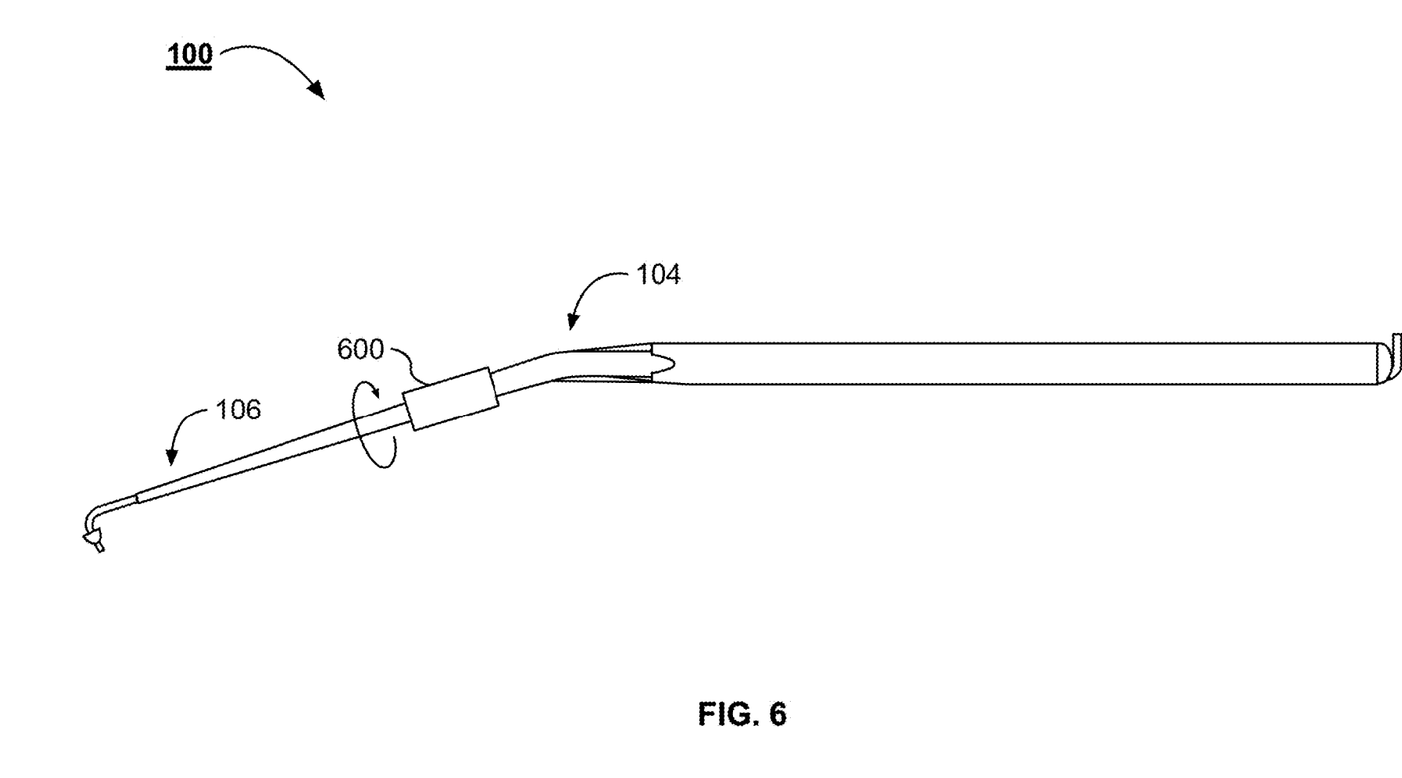
FIG. 6 illustrates an example handpiece with a compression fitting.

FIG. 6 illustrates an example handpiece 100 with a compression fitting 600. The compression fitting 600 can be knurled nut. The compression fitting 600 can couple the angled portion 104 with the tip portion 106. The compression fitting 600 can be loosened to enable the tip portion 106 to rotate with respect to the angled portion 104. Once the surgeon selects a degree of rotation, the surgeon can tighten the compression fitting 600 to lock the degree of rotation between the angled portion 104 and the tip portion 106 in place. In other implementations, the tip portion 106 and the angled portion 104 can be held together with a friction fit that enables the tip portion 106 to be rotated with respect to the tip portion 106.

Figure 7:
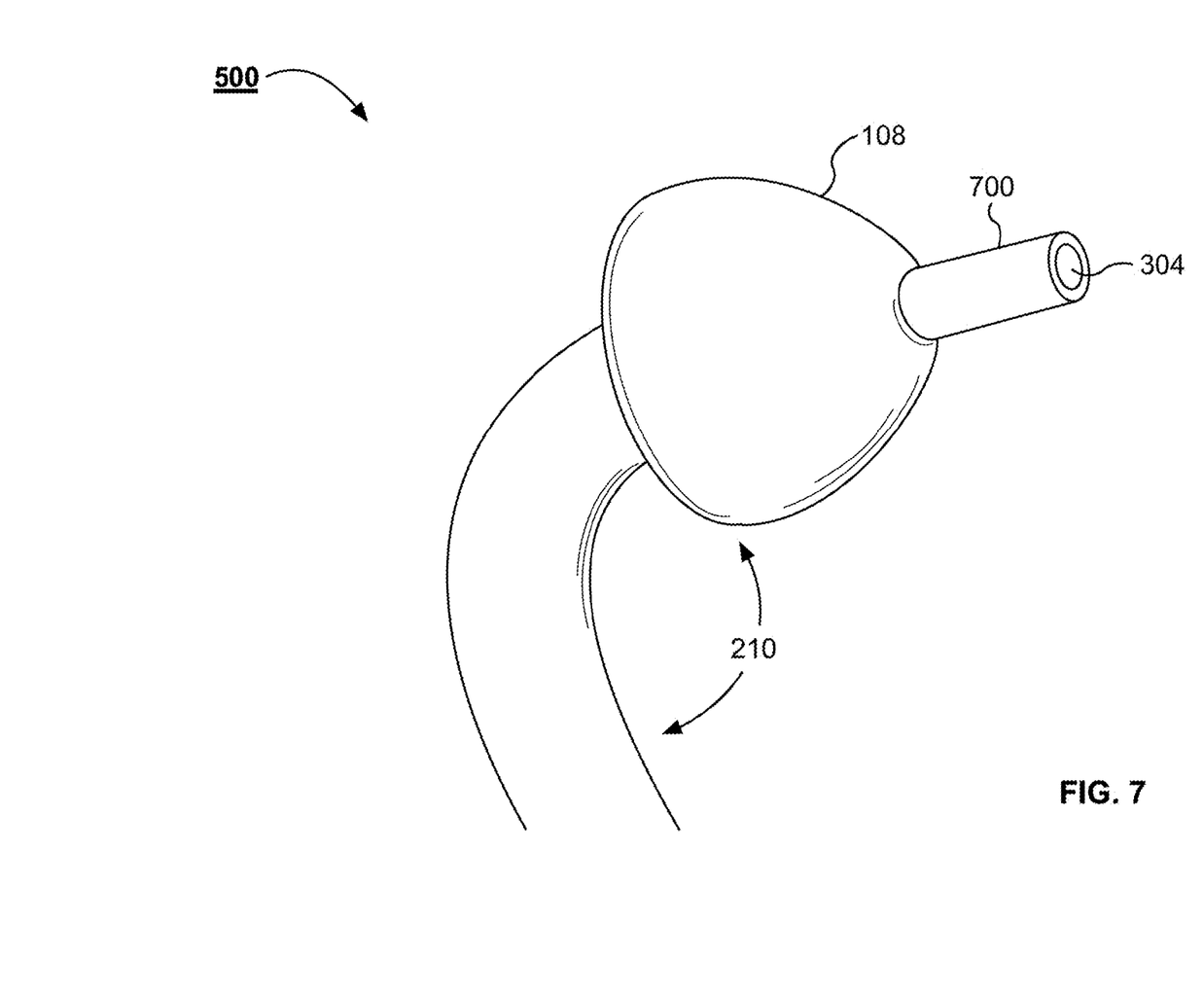
FIG. 7 illustrates an enlarged view of the tip of the example handpiece illustrated in FIG. 1.

FIG. 7 illustrates an enlarged view of the tip 500 of the example handpiece 100. The tip 500 can include a needle end 700. The needle end 700 includes the outlet 304. The needle end 700 can be a blunt end or can be beveled to form a point. The needle end 700 can be configured to pierce the round window membrane. The needle end 700 extends past the collar 108 by a length between about 1 mm and about 4 mm, between about 2 mm and about 3 mm, or between about 2.5 mm and about 3 mm. For example, the needle end 700 can have a length of 2.7 mm. The needle end 700 can have a gauge size between about 25 and about 30, between about 26 and about 30, or between about 27 and about 30. Once the collar 108 is seated into the round window only the needle end 700 projects into the cochlea. The collar 108 can control the depth the needle end 700 projects into the cochlea. The needle end 700 can prevent the needle end 700 from projecting too far into the cochlea. The needle end 700 can prevent the needle end 700 from projected too far into the cochlea and damaging the cochlea. The collar 108 can properly position the outlet 304 within the cochlea so that the therapeutic substance properly disperses through the cochlea. For example, if the outlet 304 is positioned too shallow into the cochlea, the therapeutic substance can concentrate near the round window and not disperse through the cochlea. If the outlet 304 is position too deep into the cochlea, the needle end 700 can cause damage or trauma to the cochlea. In some implementations, the tip 500 is manufactured from a malleable material such that a surgeon can bend the tip 500 to alter the angle 210. The collar 108 can be coupled with the tip 500 with an adhesive. In some implementations, the tip 500 can include a groove in which the collar 108 is seated.

Figures 8A, 8B:
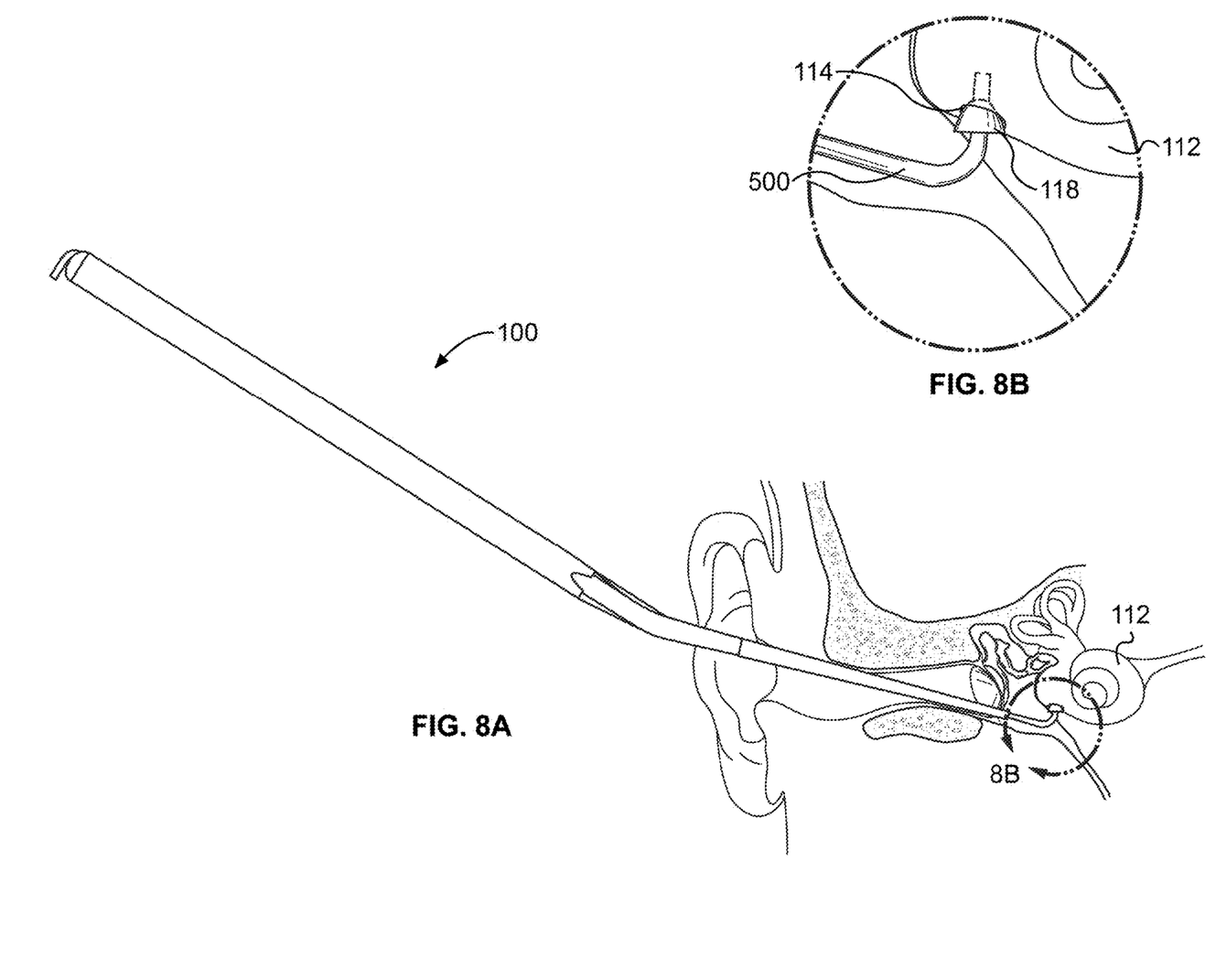
FIGS. 8A and 8B illustrates the tip of the example handpiece inserted into a round window.

FIGS. 8A and 8B illustrate the tip 500 inserted into the round window. FIG. 8A illustrates the handpiece 100 inserted through the ear canal with the tip 500 inserted into the round window 114. FIG. 8B illustrates an enlarged view, from FIG. 8A, of the tip 500 inserted into the round window 114. The tip 500 can be used to pierce the round window membrane. The tip 500 can be inserted into the round window 114. The collar 108 can be seated into the round window 114 and seal the round window 114 as fluid is injected into the cochlea 112. The collar 108 is tapered from a diameter smaller than the diameter of the round window 114 to a diameter that is wider than the diameter of the round window 114. When the collar 108 is depressed against the round window 114, the collar 108 can occlude the round window 114. The collar 108 can also be used to control the insertion depth of the tip 500 into the cochlea 112. For example, the collar 108 can prevent the tip 500 from being inserted into the cochlea past the collar 108. The portion of the collar 108 with a diameter wider than the diameter of the round window 114 can substantially stop the tip 500 from farther insertion of the tip 500 into the cochlea 112. Moving the collar 108 towards the outlet 116 of the tip 500 reduces the depth to which the tip 500 can be inserted. The collar 118 can prevent the tip 500 from being inserted too far into the cochlea 112.

Figure 9:
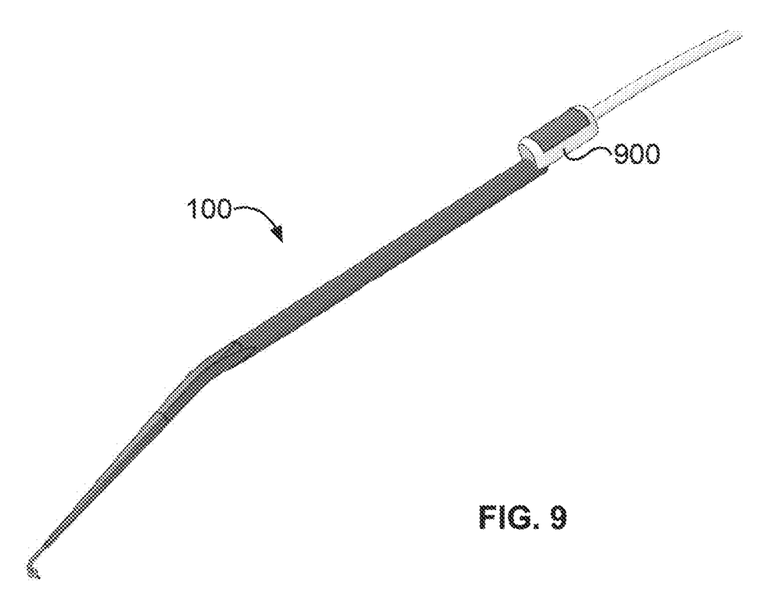
FIGS. 9 and 10 illustrate example fluid reservoirs coupled with the example handpiece illustrated in FIG. 1.
Figure 10:
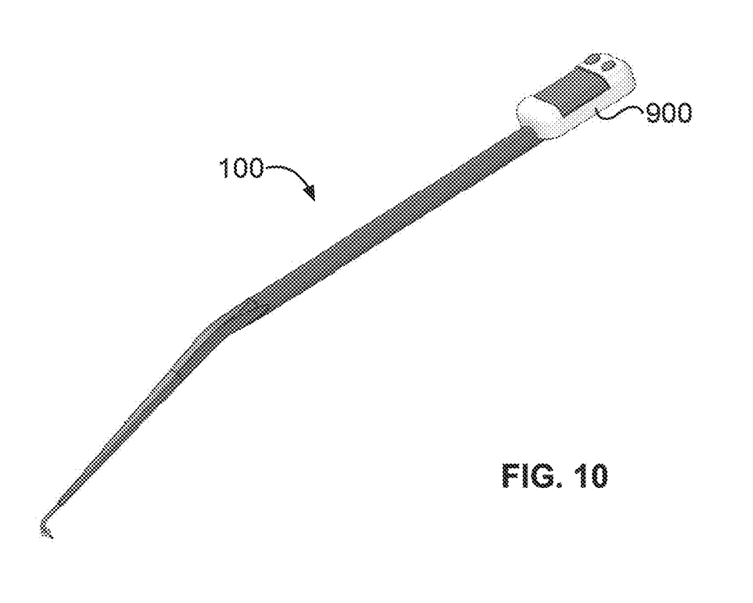

FIG. 9 illustrates an example fluid reservoir 900 coupled with the example handpiece 100. The fluid reservoir 900 can be coupled with a pump that pumps the fluid stored in the fluid reservoir 900 through the microfluidic channel 300 of the handpiece 100 and out the handpiece's outlet 304. The fluid reservoir 900 can be coupled to displacement pump, syringe, syringe pump, or other type of mechanical, electric-mechanical, hydraulic, or pneumatic-driven actuator. The inlet 302 of the microfluidic channel 300 can coupled to the fluid reservoir 900 to enable the fluid to be introduced to the microfluidic channel 300. In some implementations, the fluid reservoir 900 can be separable from the handpiece 100. The fluid reservoir 900 can include a pierceable septum that the inlet 302 pierces when a user attaches the fluid reservoir 900 to the handpiece 100. In other implementations, the fluid reservoir 900 can be a component of the handpiece 100 that is filled with a fluid prior to use. The fluid reservoir 900 can include a pierceable septum through which the fluid reservoir 900 is loaded. For example, a syringe can be loaded with the therapeutic substance. The syringe's needle can be inserted through the pierceable septum and the therapeutic substance injected into the fluid reservoir 900. FIG. 10 illustrates an example fluid reservoir 900 coupled with a handpiece 100. The fluid reservoir 900 can include self-contained pumping system. The self-contained pumping system can pump a fluid from the fluid reservoir to the outlet 304.

Figure 11:
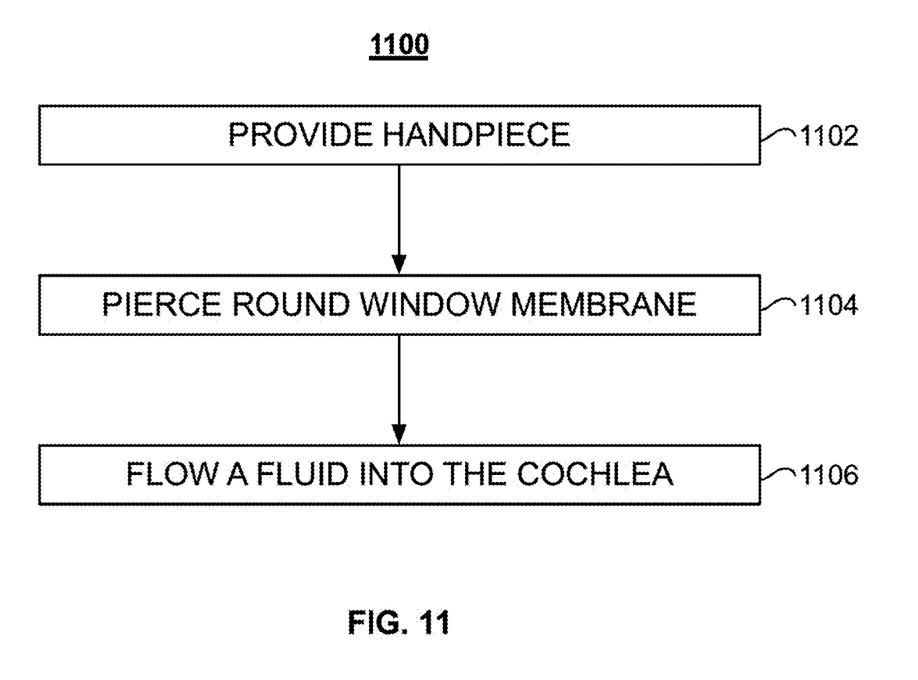
FIG. 11 illustrates a block diagram of an example method to flow a fluid into the cochlea with the example handpiece illustrated in FIG. 1.

FIG. 11 illustrates a block diagram of an example method 1100 to flow a fluid into the cochlea. The method 1100 can include providing a handpiece (ACT 1102). The method 1100 can include piercing a round window membrane (ACT 1104). The method 1100 can include flowing a fluid into the cochlea (ACT 1106).

As set forth above, the method 1100 can include providing a handpiece (ACT 1102). The handpiece 100 can be any of the handpieces described herein. For example, the handpiece 100 can include a tool shaft that includes a first distal end, a first proximal end, a first fluidic channel, and a first longitudinal axis. The handpiece 100 can include an angled portion that can include a second distal end, a second proximal end coupled with the first distal end, a second fluidic channel in communication with the first fluidic channel, and a second longitudinal axis defining an obtuse angle with the first longitudinal axis. The handpiece 100 can include a tip portion projecting from the angled portion and comprising an outlet and a third fluidic channel in communication with the second fluidic channel. The handpiece 100 can include a collar coupled with the tip portion.

The method 1100 can include piercing a round window membrane (ACT 1104). The round window membrane can be pierced with the tip portion of the handpiece 100. For example, the provided handpiece 100 can be inserted through the ear canal. The handpiece's angled portion 104 can be configured to enable transcanal access of the round window. The tip 500 of the tip portion 106 can be angled to position the needle end 700 substantially perpendicular to the round window and round window membrane. The needle end 700 can be pressed against the round window membrane to pierce the round window membrane. The collar 108 can prevent the needle end 700 from projecting too far into the cochlea and causing damage to the cochlea. The collar 108 can seat into the round window to seal the round window as the fluid is injected into the cochlea. Based on the patient's anatomy, a surgeon can set a rotational offset between the tip portion and the angled portion of the handpiece 100 to enable the needle end 700 to access the round window. Also based on the patient's anatomy, the surgeon can set the angle 210 between the needle end 700 and the tip portion such that the outlet 304 is positioned substantially perpendicular to the round window and round window membrane. CT or MRI scans of the patient's middle and inner ear can be conducted. The surgeon can measure the anatomical angles of the patient's inner and middle ear to select the angle 210 of the tip portion 106. Also, based on the CT or MRI scans the surgeon can select the length of the needle end 700 such that when the collar 108 is seated into the round window the outlet 304 is properly positioned within the cochlea. The proper position of the outlet 304 can be a depth into the cochlea that does not cause damage to the cochlea but enables distribution of the fluid through the cochlea.

The method 1100 can include flowing a fluid into the cochlea (ACT 1106). A pump can pump the fluid from a fluid reservoir 900, through the microfluidic channel 300, and into the cochlea via outlet 304. In some implementations, the pump can be external to the handpiece 100. In other implementations, fluid reservoir 900 can include a self-contained pump that pumps the fluid from the fluid reservoir 900 to the outlet 304. The method 1100 can include drilling, or otherwise forming, a ventilation hole in the stapes footplate. The ventilation hole can enable the release of pressure from the cochlea as the pump flows the fluid into the cochlea.

CONCLUSION

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A handpiece to deliver a fluid to an ear, comprising:
a tool shaft comprising a first distal end, a first proximal end, a first fluidic channel;
a tip portion coupled with the tool shaft and comprising an outlet and a second fluidic channel in communication with the first fluidic channel;
an angled portion between the tool shaft and the tip portion and configured to rotate with respect to the tool shaft; and
a collar coupled with the tip portion a predetermined distance from the outlet, the collar configured to seat with a round window and control a distance the tip portion projects into a cochlea.

2. The handpiece of claim 1, wherein the angled portion comprises a second distal end, a second proximal end coupled with the first distal end, a third fluidic channel in communication with the first fluidic channel, and a first longitudinal axis defining an angle with a second longitudinal axis of the tool shaft configured for trans-canal positing of the tip portion at the round window.

3. The handpiece of claim 2, wherein the angle is between about 140° and about 170°.

4. The handpiece of claim 2, wherein the tip portion projects from the angled portion at an angle between about 75° and about 130°.

5. The handpiece of claim 2, wherein the tip portion projects from the angled portion at an angle between about 110° and about 120°.

6. The handpiece of claim 1, further comprising a fluid reservoir in communication with the outlet via the first fluidic channel and the second fluidic channel.

7. The handpiece of claim 6, the fluid reservoir further comprising a pierceable septum configured to enable filling of the fluid reservoir.

8. The handpiece of claim 1, further comprising:
a fluid reservoir; and
a self-contained pumping system coupled with the tool shaft and configured to pump a fluid from the fluid reservoir to the outlet.

9. The handpiece of claim 1, wherein the first fluidic channel and the second fluidic channel form a fluid channel.

10. The handpiece of claim 1, wherein the tip portion is configured to rotate with respect to the tool shaft.

11. The handpiece of claim 1, wherein the collar is substantially dome shaped.

12. The handpiece of claim 1, wherein the first fluidic channel is encased within the tool shaft and the second fluidic channel is encased within the tip portion.

13. The handpiece of claim 1, wherein each of the first fluidic channel and the second fluidic channel are encased in a sterilizable plastic.

14. A handpiece to deliver a fluid to an ear, comprising:
a tool shaft comprising a first distal end, a first proximal end, a first fluidic channel;
a tip portion coupled with the tool shaft and comprising an outlet and a second fluidic channel in communication with the first fluidic channel, the tip portion is configured to detach from the tool shaft; and
a collar coupled with the tip portion a predetermined distance from the outlet, the collar configured to seat with a round window and control a distance the tip portion projects into a cochlea.

15. A method comprising:
providing a handpiece comprising:
a tool shaft comprising a first distal end, a first proximal end, a first fluidic channel;
a tip portion coupled with the tool shaft and comprising an outlet and a second fluidic channel in communication with the first fluidic channel; and
a collar coupled with the tip portion a predetermined distance from the outlet, the collar configured to seat with a round window and control a distance the tip portion projects into a cochlea;
piercing a round window membrane covering the round window with the tip portion;
setting a rotational offset between the tip portion and an angled portion of the handpiece; and flowing a fluid through the outlet and into the cochlea via the first fluidic channel and the second fluidic channel.

16. The method of claim 15, further comprising forming a ventilation hole in a stapes footplate.

17. The method of claim 15, further comprising flowing, by a self-contained pumping system coupled with the tool shaft, the fluid from a reservoir.

18. The method of claim 15, further comprising seating the collar in the round window.

\* \* \* \* \*